(12) United States Patent
Bar-Shavit et al.

(10) Patent No.: US 8,835,390 B2
(45) Date of Patent: Sep. 16, 2014

(54) MODULATION OF OSTEOCLAST DIFFERENTIATION

(75) Inventors: Zvi Bar-Shavit, Jerusalem (IL); Refael Aharon, Modi'in (IL)

(73) Assignee: Osteobuild Ltd., Jerusalem (IL)

( * ) Notice: Subject to any disclaimer, the term of this patent is extended or adjusted under 35 U.S.C. 154(b) by 1531 days.

(21) Appl. No.: 11/992,234

(22) PCT Filed: Sep. 19, 2006

(86) PCT No.: PCT/IL2006/001095
§ 371 (c)(1),
(2), (4) Date: Feb. 16, 2011

(87) PCT Pub. No.: WO2007/034477
PCT Pub. Date: Mar. 29, 2007

(65) Prior Publication Data
US 2012/0238501 A1    Sep. 20, 2012

Related U.S. Application Data

(60) Provisional application No. 60/717,762, filed on Sep. 19, 2005.

(51) Int. Cl.
| | | |
|---|---|---|
| *A61P 19/08* | (2006.01) | |
| *A61P 19/10* | (2006.01) | |
| *A61P 1/02* | (2006.01) | |
| *A61K 31/05* | (2006.01) | |
| *C07C 39/00* | (2006.01) | |
| *A61K 31/12* | (2006.01) | |

(52) U.S. Cl.
CPC ..................................... *A61K 31/12* (2013.01)
USPC ......... 514/16.7; 514/16.8; 514/679; 435/377; 568/325

(58) Field of Classification Search
None
See application file for complete search history.

(56) References Cited

U.S. PATENT DOCUMENTS

2004/0213782 A1* 10/2004 Wax ........................... 424/143.1

FOREIGN PATENT DOCUMENTS

WO    WO 03/037315    *    5/2003

OTHER PUBLICATIONS

Loitto et al., J. Leukoc. Biol., 2002, vol. 71:212-222.*
International Search Report mailed on Mar. 14, 2007 for International Application No. PCT/IL2006/001095.
Vaananen K. Mechanism of osteoclast mediated bone resorption—rationale for the design of new therapeutics, Advance Drug Delivery Reviews 57 (2005), pp. 959-971.
Gaspare De Santo Natale et al, Renal function in space: the link between osteoporosis, hypercalciuria, and aquaporins, Journal of Renal Nutrition, vol. 15, No. 1, Jan. 2005, pp. 183-188.
Tsukaguchi et al, Molecular characterization of a broad selectivity neutral solute channel, The Journal of Biological Chemistry, vol. 273, No. 38, Sep. 18, 1998, pp. 24737-24743.
Tsukaguchi et al, Functional and molecular characterization of the human neutral solute channel aquaporin -9, The American Physiological Society, vol. 277, No. 5, Nov. 1999, pp. F685-F696.
Yasuda et al, osteoclast differentiation factor is a ligand for osteoprotegerin/osteoclastogenesis-inhibitory factor and is identical to TRANCE/TANKL, Proceedings of the national academy of sciences of USA, vol. 95, Mar. 1998, pp. 3597-3602.
Aharon R. et al, Involvement of aquaporin 9 in osteoclast differentiation, The Journal of Biological Chemistry, vol. 281, No. 28, Jul. 14, 2006, pp. 19305-19309.
Aharon R. et al, Aquaporin 9 plays a role in osteoclast differentiation, Journal of Bone and Mineral Research, vol. 20, No. 9, suppl. 1, Sep. 2005, p. S253.
Suda T. et al, Modulation of osteoclast differentiation and function by the new members of the tumor necrosis factor receptor and ligand families, Endocrine Reviews, vol. 20, No. 3, 1999, pp. 345-357.
Teitelbaum S. L., Bone resorption by osteoclasts, Science, vol. 289, Sep. 1, 2000, pp. 1504-1508.
Teitelbaum S. L. et al, Genetic regulation of osteoclast development and function, Nature Reviews Genetics, Aug. 2003, vol. 4, pp. 638-649.
Lacey D. L. et al, Osteoprotegerin ligand is a cytokine that regulates osteoclast differentiation and activation,Cell, Apr. 17, 1998, vol. 93, pp. 165-176.
Preston G. M. et al, Appearance of water channels in *Xenopus oocytes* expressing red cell CHIP28 protein, Science, vol. 256, Apr. 17, 1992, pp. 385-387.
King L. S. et al, From structure to disease: the evolving tale of aquaporin biology, Nature Reviews—Molecular Cell Biology, vol. 5, Sep. 2004, pp. 687-698.
Maurel, Aquaporins and water permeability of plant membranes, Annu. Rev. Plant Physiol. Plant Mol. Biol., vol. 48, 1997, pp. 399-429.
Mobasheri A. et al, Aquaporin water channels AQP1 and AQP3, are expressed in equine articular chondrocytes, The Veterinary Journal, vol. 168, 2004, pp. 143-150.
Agre P. et al, Aquaporin water channels—from atomic structure to clinical medicine, Journal of Physiology, 2002, Vo. 542, No. 1, pp. 3-16.
Soren Nielsen et al, Physiology and pathophysiology of renal aquaporins, J Am Soc Nephrol, 1999, vol. 10, pp. 674-663.
Christa M. et al, New potent inhibitors of aquaporins: silver and gold compounds inhibit aquaporins of plant and human origin, FEBS Letters, 2002, vol. 531, pp. 443-447.
Tran et al, Aquaporins 6-12 in the human eye, Acta Ophthalmologica, 2012, pp. 1-7.
Aharon et al, Involvement of aquaporin 9 in osteoclast differentiation, The Journal of Biological Chemistry, Jul. 14, 2006, vol. 281, No. 28, pp. 19305-19309.

* cited by examiner

*Primary Examiner* — Xiaozhen Xie
(74) *Attorney, Agent, or Firm* — Vorys, Sater, Seymour and Pease LLP; Susanne M. Hopkins (57) ABSTRACT

The present invention concerns the use of an aquaprin-9 (AQP-9) modulator for the preparation of a pharmaceutical composition for treating or preventing a pathological condition associated with unbalanced osteoclast differentiation. In accordance with one embodiment, the modulator is an AQP-9 inhibitor. An example of AQP-9 inhibitor is phloretin which has been shown to inhibit osteoclast differentiation, following induction of bone marrow cells with RANKL. The invention also concerns methods for modulating osteoclast differentiation, methods for prevention and treating pathological conditions associated with unbalanced osteoclast differentiation as well as pharmaceutical composition comprising such modulators.

10 Claims, 3 Drawing Sheets

MODULATION OF OSTEOCLAST DIFFERENTIATION

This Application is a National Stage of International Application No.: PCT/IL2006/001095, filed on Sep. 19, 2006, which claims the benefit of U.S. Provisional Patent Application Ser. No. 60/717,762, filed on Sep. 19, 2005, the entire content of which is hereby incorporated by reference in its entirety.

FIELD OF THE INVENTION

This invention relates to bone remodeling processes and in particular to osteoclast differentiation.

LIST OF PRIOR ART

1. Suda, T., et al. (1999) *Endocr. Rev.* 20, 345-357;
2. Teitelbaum, S. L. (2000) *Science* 289:1504-1508;
3. Teitelbaum, S. L., and Ross, F. P. (2003). *Nat Rev Genet.* 4:638-649;
4. Lacey, D. L., et. al. (1998) *Cell* 93:165-176;
5. Yasuda, H., et al. (1998). *Proc. Natl. Acad. Sci. USA.* 95:3597-3602;

BACKGROUND OF THE INVENTION

Aquaporins

The discovery of aquaporins (water channels) in 1992 by Agre and colleagues [Preston, G. M., et al. (1992) *Science* 256, 687-698] dramatically changed the concept of regulation of water transport through biological membranes. Aquaporins are ~30 kDa tetrameric proteins [King, L. S., et al. (2004) *Nat. Rev. Mol. Cell. Biol.* 5, 800-806] characterized by six transmembrane-spanning helices, and both termini are cytosolic. Aquaporins are expressed across all organisms and control water transport in all cells [Maurel, C. (1997) Annu. Rev. Plant Physiol. Plant Mol. Biol. 48, 399-429; Mobasheri, A., et al. (2004) *Vet. J.* 168, 143-150; Agre, P., et al. King, L. S (2002) *J. Physiol.* 1, 3-16]. Eleven mammalian aquaporins have been identified so far and they have cellular and subcellular distributions in different organs that indicate probable functional roles. Studies in animals and humans have revealed that aquaporins participate in a wide range of physiological and pathological processes.

Osteoclasts

Osteoclast is the principal, if not the exclusive, resorptive cell of bone, playing a central role in the formation, growth and remodeling of the skeleton. This multinucleated cell is formed by the fusion of mononuclear progenitors of the monocyte/macrophage family [Suda, T., et al. (1999) *Endocr. Rev.* 20, 345-357; Teitelbaum, S. L. (2000) *Science* 289:1504-1508; Teitelbaum, S. L., and Ross, F. P. (2003). *Nat Rev Genet.* 4:638-649]. The differentiation of the osteoclast from its precursor cells requires the presence of osteoblasts or marrow stromal cells [Suda, T., (1999) ibid.]. Two factors, macrophage colony-stimulating factor (M-CSF) and receptor activator of nuclear factor kappa B (NF-κB) (RANK) ligand (RANKL), expressed by the accessory cells are essential and sufficient to promote osteoclastogenesis [Lacey, D. L., et. al. (1998) *Cell* 93:165-176; Yasuda, H., et al. (1998). *Proc. Natl. Acad. Sci. USA.* 95:3597-3602]. Excessive osteoclastic activity leads to progressive loss of bone mass causing weakening of the skeleton, manifested by a variety of pathological conditions such as osteoporosis. Reduced osteoclast activity results in the formation of overly dense bones, as found in osteopetrosis. Thus, regulation of osteoclastogenesis plays an important role in maintaining a healthy skeleton.

SUMMARY OF THE INVENTION

It has now been shown that a member of the aquaporin (aquaglyceroporin) family, AQP-9, plays a role in the differentiation of the bone-resorbing cell, the osteoclast. Specifically, the present invention is based on the finding that expression of aquaporin 9 (AQP-9) is increased in osteoclasts and precursors thereof and that this increased expression leads to osteoclast differentiation. Further, the invention is based on the finding that in the presence of an AQP-9 inhibitor, phloretin, the size or number of osteoclasts or number of nuclei in an osteoclast is reduced. Thus, it was envisaged by the inventors that AQP-9 inhibitors may have a therapeutic beneficial effect in pathological conditions associates with osteoclast formation and differentiation, such as diseases and conditions manifested excessive bone loss.

Thus, in accordance with a first of its aspects, the present invention provides for the use of an aquaprin-9 (AQP-9) modulator for the preparation of a pharmaceutical composition for treating or preventing a pathological condition associates with unbalanced osteoclast differentiation.

In accordance with one embodiment, the "inhibitory embodiment", the invention provides the use of an aquaprin-9 (AQP-9) inhibitor for the preparation of a pharmaceutical composition for treating or preventing a pathological condition associates with unbalanced osteoclast differentiation.

In accordance with another embodiment, the "inducing embodiment", the invention provides the use of an aquaprin-9 (AQP-9) inducer for the preparation of a pharmaceutical composition for treating or preventing a pathological condition associates with unbalanced osteoclast differentiation.

The invention also provides a method for modulating unbalanced osteoclast differentiation, the method comprising providing osteoclasts, osteoclast precursor cells or a mixture of same with an amount of an AQP-9 modulator, the amount of said modulator being effective to affect AQP-9 activity in said osteoclast cells or said precursor cells. In accordance with the inhibitory embodiment, the modulator is an AQP-9 inhibitor for inhibiting AQP-9 activity, while in accordance with the inducing embodiment; the modulator is an AQP-9 inducer, for inducing AQP-9 activity.

In accordance with a third aspect, the present invention provides a method for treating or preventing in a subject a pathological condition associates with unbalanced osteoclast differentiation, the method comprises providing said subject with an amount an AQP-9 modulator, the amount of said AQP-9 modulator being effective to affect AQP-9 activity in said unbalanced osteoclasts. In accordance with the inhibitory embodiment, the method provides treatment of prevention of a pathological condition associated with increased osteoclast differentiation, while in accordance with the inducing embodiment; the method provides treatment or prevention of a pathological condition associated with osteoclast deficiency.

Finally, in accordance with a fourth aspect, the invention provides a pharmaceutical composition for the treatment of prevention of a pathological condition associates with unbalanced osteoclast differentiation, the composition comprising as an active ingredient an amount of AQP-9 modulator, the amount of said AQP-9 modulator being effective to affect AQP-9 activity in osteoclast cells or osteoclast precursor cells.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

The differentiation of the osteoclast includes fusion of mononuclear precursors to form the multinucleated osteoclast. Upon fusion of the precursors, the volume of the mature osteoclast increases more dramatically than its surface, resulting in the addition of new cytosol into the cells. Water, being the major cytosolic component led to the understanding that aquaporin(s) are associated with the enhanced water influx.

The inventors have found that following induction of RANKL, a ligand associated with osteoclast differentiation, there was an increased expression AQP-9 and that this increase in expression precedes osteoclast precursor fusion. This finding led to the understanding that the water channel plays a role in the formation of a large multinucleated osteoclast, probably, by mediating rapid water influx to enable the increase in cell volume and that preventing this rapid water influx may inhibit osteoclast formation or lead to the dehydration of osteoclasts which is followed by a decrease in their size, thereby preventing uncontrolled effects of osteoclast formation.

Thus, in its broadest aspect, the present invention concerns the use of one or more modulators of the AQP-9 for the preparation of a pharmaceutical composition for treating or preventing a pathological condition associates with unbalanced osteoclast differentiation. As appreciated, while the invention is described in the following detailed description with reference to the above use, it is to be understood that also encompassed within the present invention methods for modulating osteoclast differentiation making use of the AQP-9 modulator; methods of treating or preventing a pathological condition comprising providing a subject in need of treatment an amount is of the modulator; as well as pharmaceutical compositions comprising as the active principle ingredient (API) AQP-9 modulator.

For the purpose of understanding the invention the following terms are used and should be understood as comprising the indicated meaning:

AQP-9 modulator—Aquaporins (AQPs) are membrane water channels that play critical roles in controlling the water contents of cells. More than eleven different AQPs have been found in human body, and several diseases, and are sequentially numbered as AQP-0 to AQP-9. Thus, the term "AQP-9 modulator" is used herein to denote any agent, being a polymeric substance, of high or medium (e.g. oligomer) molecular weight, or a small molecular weight compound which has a statistically significant affect the water/glycerol transferring activity of the AQP-9 channel in a treated experiment (i.e. either in vivo or in vitro) as compared to the untreated control. The effect on AQP-9 channel activity may be exhibited by a change in osteoclast formation/differentiation in the treated experiment, which may be determined by measuring a change in one or more member of the following parameters: number of formed osteoclasts, size of formed osteoclasts, and number of nuclei in an osteoclast in a treated experiment. The change may be an increase or a decrease in one or more of said parameters. It is noted that when the effect comprises a decrease in number or size, it does not necessarily mean complete abolishment of any formation, or growth in size or number of nuclei.

AQP-9 inhibition or AQP-9 inhibitor—refers to any agent as defined above, wherein the modulation is exhibited by a statistically significant decrease in the water/glycerol transferring activity of the aqauproin-9 channel as compared to an untreated control. This term does not necessarily mean abolishment of the AQP-9 activity.

AQP-9 channel blockers—refers to any agent that may block directly the channel and thus prevent or decrease its water/glycerol transferring properties. Examples of such agents are phloretin (2',4',6'-Trihydroxy-3-(4-hydroxyphenyl)-propiophenone, mercury, cytoskeletal inhibitors were shown to play a role in insertion of AQP-2 to membranes and the microtubular network has been implicated in this process. Both vanadate, a rather nonspecific inhibitor of ATPases, and erythro-9(3-(2-hydroxynonyl))adenine, a relatively specific inhibitor of dynein, inhibit the antidiuretic response in toad bladder (All inhibitors cited from: J Am Soc Nephrol 10:647-663, 1999); silver and gold compounds (FEBS Lett. 2002 Nov. 20; 531(3):443-7.).

Antibodies from circulating blood may be directed to the active site of AQP-9 (i.e. to the protein's loops that are exposed at the surface of the cell).

AQP-9 expression/translation reducing agents—refers to any agent that may affect AQP-9 activity by reducing the expression of the AQP-9 gene (for example by using antisense to the gene or antisense to the mRNA); by decreasing the amount of mRNA available for translation (by using siRNA against the mRNA; by using ribozymes capable of specifically degrading the AQP-9 mRNA, by using microRNA). In all the above "expression reducing agents", the agents may be administered to the cells directly ("naked" siRNA etc) or may be introduced into the cells together with transfection agents. The "expression reducing agents" may also be introduced into the cells via expression vectors enabling their expression and production inside the cell.

AQP-9 induction or AQP-9 inducer—refers to any agent as defined above, wherein the modulation is exhibited by a statistically significant increase in the water/glycerol transferring activity of the aqauproin-9 channel as compared to an untreated control.

Osteoclast differentiation—which may be used interchangeably with the term "osteoclast formation" refers to the process osteoclast precursor (progenitor) cells are recruited from haematopoietic compartments, and then proliferate and differentiate toward mature osteoclasts. During this multistep differentiation process postmitotic osteoclast precursors progressively express osteoclast-associated markers, such as cathepsin-K, MMP-9, calcitonin receptor and tartrate-resistant acid phosphatase (TRAP), while, losing some of their macrophage characteristics. Then, mononuclear preosteoclasts fuse together to form multinucleated giant cells. Terminal osteoclast differentiation eventually leads to active bone-resorbing cells. Once formed, the osteoclast may be referred to as large osteoclasts which are typically those characterized by a plurality of nuclei (up to several dozens) or small osteoclasts containing few nuclei (as few as three).

Unbalanced osteoclast differentiation—refers to a condition of unbalanced bone remodelling in which bone resorption is followed by new bone formation, thereby maintaining mechanical strength and structure of an adults skeleton. This process couples the balanced formation of osteoclasts which are known as the bone-resorbing cells and osteoblasts, known as the bone-forming cells (which are of mesenchymal origin). Thus, the term "unbalanced osteoclast differentiation" denotes any condition where this delicate balance between osteoclasts and osteoblasts formation is disrupted. Such disruption may results either in an undesired increase or in an undesired decrease in the number and/or size osteoclasts as well as to an increase or decrease in the number of nuclei in an osteoclast.

Treatment or prevention—and the like are used herein to refer to obtaining a desired pharmacological and physiological effect. The effect may be prophylactic in terms of preventing or partially preventing a disease, symptom or pathological condition and/or may be therapeutic in terms of a partial or complete cure of a disease, condition, symptom or adverse effect attributed to a pathological condition. Thus, "treatment" covers any treatment of a disease in a mammal, particularly a human, and includes: (a) preventing a pathological condition from occurring in an individual which may be predisposed to develop a pathological condition but has not yet been diagnosed as having it, i.e., causing the clinical symptoms of a pathological condition not to develop in a subject that may be predisposed to develop the condition but does not yet experience or display symptoms of the condition; (b) inhibiting, i.e., arresting or reducing the development of the pathological condition or its clinical symptoms; or (c) relieving symptoms associating with the pathological condition The term "pathological condition" used herein denotes any condition which is associated with unbalanced osteoclast formation and differentiation, which requires for improving the well-being of the subject the delivery of an AQP-9 modulator (being an inhibitor or an inducer thereof, as defined hereinbefore). This includes, inter alia, any condition which requires the reduction or induction of osteoclast formation/differentiation so as to affect the process of bone formation in said subject. In accordance with one aspect of the invention, the pathological condition is associated with the formation/differentiation of osteoclasts at a rate which is higher than the rate of osteoblast formation (i.e. an increased osteoclast formation). Such an increased osteoclast formation may lead to excessive bone resorption. In accordance with another aspect of the invention, the pathological condition is associated with the formation/differentiation of osteoclasts at a rate which is lower than the rate of osteoblast formation (i.e. a reduced osteoclast formation). Reduced osteoclast formation may lead to overly dense bone.

As indicated above, the AQP-9 modulator may be an AQP-9 inhibitor or AQP-9 inducer.

In accordance with the inhibitory embodiment, AQP-9 inhibitor may be an AQP-9 channel blocker, an AQP-9 expression inhibitor, an AQP-9 translation inhibitor, or activity blocking antibody, modified or non-modified AQP-9 like proteins. One non-limiting example of an AQP-9 channel blocker is phloretin or a functional derivative thereof (e.g. a chemical derivative of phloretin that has essentially a similar inhibitory effect on AQP-9).

The AQP-9 inhibitor may be used for preparing a pharmaceutical composition for the treatment or prevention of a pathological condition associated with excessive bone resorption. A non-limiting list of conditions known to be involved with excessive bone resorption include, without being limited thereto, osteoporosis, an inflammation-associated bone disease, a cancer-associated bone disease, an infection-associated bone disease, periodontal disease, Paget's disease.

Osteoporosis is characterized by a reduction in bone mass and deterioration in bone architecture. The most common cause of osteoporosis in women is loss of estrogen, which occurs at menopause. The increase in bone loss is mediated by an increase in osteoclast number and size. Current therapies for osteoporosis include estrogen and Selective Estrogen Receptor Modulators (SERMs), which inhibit osteoclast differentiation, and bisphosphonates, which inhibit osteoclastic bone resorption.

Rheumatoid arthritis (RA) is a chronic inflammatory disease characterized by focal regions of subchondral osteoclastic bone resorption. Subjects having RA are at risk for development of a generalized form of bone loss. Macrophages, which are capable of differentiating into osteoclasts, accumulate in the rheumatoid synovial membrane in the inflammatory state. Human synovial fibroblasts and T-cells, which have been shown to express RANKL, are also present in the rheumatoid joint. T-cells from rheumatoid patients are capable of supporting osteoclast differentiation from hematopoietic cells without the participation of other cells.

Cancer-associated bone diseases which may be understood interchangeably with the term malignant bone diseases may be any pathological condition involved with hyperproliferation and which are manifested in association with AQP-9 activity, such as, without being limited thereto, multiple myeloma, humoral hypercalcemia of malignancy, and tumor metastasis, all of which are currently treated with inhibitors of bone resorption. Bisphosphonates, which inhibit osteoclastic bone resorption, have been shown to decrease skeletal events in patients with multiple myeloma and those with bone metastases from breast cancer, as well as correcting hypercalcemia in cancer.

Infection associated bone diseases refer to any pathological condition where an infection causes unbalanced osteoclast or osteoblast differentiation. A non-limiting example is osteomyelitis which is an acute or chronic inflammatory process of the bone and its structures secondary to infection with pyogenic organisms. The infection associated with osteomyelitis may be localized or it may spread through the periosteum, cortex, marrow, and cancellous tissue. The bacterial pathogen varies on the basis of the patient's age and the mechanism of infection.

Periodontal disease in humans is characterized by alveolar bone destruction and tooth loss. Periodontitis is implicated in the increased risk of systemic diseases such as heart failure, stroke and bacterial pneumonia. Bacterial infections and their associated immunological response contribute to the bone loss associated with periodontitis. However, the mechanisms behind this disorder are not clearly understood. This term should be understood to also include aseptic loosening of prosthetic implants and the like.

Paget's disease of bone is characterized by local regions of increased osteoclast numbers and activity. The increase in bone resorption is compensated by an increase in bone formation and local bone turnover; however, the newly formed bone is abnormally weak and prone to fracture or bowing. Bisphosphonates and calcitonin are used clinically to treat the increased bone resorption in Paget's disease.

The AQP-9 inducer may be used for the preparation of a pharmaceutical composition for the treatment or prevention of a pathological condition associated with osteoclast deficiency which may result in overly dense bones. Without being limited thereto, an example of such a condition is osteopetrosis, which is an inherited disorder, characterized by an increase in bone density. In severe forms the bone marrow cavity may be obliterated. Long-term therapy with interferon gamma has been shown to increase bone resorption and hematopoiesis and improves leukocyte function.

The invention also concerns a method of modulating unbalanced osteoclast differentiation. The method comprising providing osteoclasts (large and/or small), osteoclast precursor (progenitor) cells or a mixture of same with an amount of an AQP-9 modulator, the amount of said modulator being effective to affect AQP-9 activity in said osteoclast cells or said precursor cells.

The method of the invention may be performed in vitro, e.g. for research purposes, or in vivo, for therapeutic purposes. An effect on the AQP-9 activity may be exhibited by measuring a change in one or more of the following parameters:

in size of osteoclasts;
in number of osteoclasts; and
in number of nuclei in a osteoclast;

When the AQP-9 modulator is an AQP-9 channel blocker, it preferable that the blocker is selectively introduced to the bone marrow of a treated subject. This can be performed by choosing injection to the blood stream or direct administration to the marrow, or by oral administration. The modulator may be conjugated or complexed to targeting moieties which selectively target osteoclast precursors/osteoclasts.

When a subject is to be treated with an AQP-9 expression reducing or translation inhibiting agents it is preferable that the latter is either targeted to the bone marrow, either by the direct administration to the bone marrow or by complexing/conjugation the expression reducing agent, or the respective expression vectors, to chemical entities capable of selectively targeting osteoclast precursors or against osteoclasts.

Examples of such targeting agents are either antibodies to the marker CD11b (Fujikawa Y, Sabokbar A, Neale S, Athanasou N A. 1996. Human osteoclast formation and bone resorption by monocytes and synovial macrophages in rheumatoid arthritis. Ann Rheum Dis. 55:816-822) or CD14 (Husheem M, Nyman J K, Vaaraniemi J, Vaananen H K, Hentunen T A. 2005. Characterization of circulating human osteoclast progenitors: development of in vitro resorption assay. Calcif Tissue Int. 76:222-230)

Another option is chemical entities such as antibodies that bind to osteoclasts themselves which will prevent the formation of larger osteoclasts. Preferably these are agents which bind osteoclast markers such as antibodies against $\alpha v \beta 3$.

By another option the selectivity to the osteoclast precursors may be not by the administration/targeting but rather by placing the sequences coding for the AQP-9 expression-reducing agent (such as antisense, siRNS. Ribozyme) under the expression control of a promoter that is selectively in osteoclast precursors such as the TRAP or cathepsin K promoters.

When administered a subject, it is preferable that the AQP-9 modulator is formulated together with a pharmaceutically and physiologically acceptable carrier to form an appropriate pharmaceutical composition. The amount of the AQP-9 modulator within the composition is such that a therapeutic effect is manifested (so as to treat or prevent a pathological condition associates with unbalanced osteoclasts formation). To this end, the subject in need of treatment is administered with an amount of the AQP-9 modulator, the amount of said AQP-9 modulator being effective to affect AQP-9 activity in said unbalanced osteoclasts.

A pharmaceutically and physiologically acceptable carrier refers to any excipient that is useful in preparing a pharmaceutical composition or formulation that is generally safe, non-toxic and neither biologically nor otherwise undesirable, and includes a carrier that is acceptable for veterinary use as well as human pharmaceutical use. The carrier may at times have the effect of the improving the delivery or penetration of the AQP-9 modulator to the target cell, for improving the stability of the modulator, for slowing clearance rates, for imparting slow release properties, for reducing undesired side effects etc. The carrier may also be a substance that stabilizes the composition (e.g. a preservative), for providing the composition with an edible flavor, etc. The carrier will be selected based on the desired form of the composition and the modulator to be included therein. For examples of carriers, stabilizers and adjuvants, see E. W. Martin, REMINGTON'S PHARMACEUTICAL SCIENCES, MacK Pub Co (June, 1990).

In accordance with one embodiment of the invention, the carrier is suitable for administration of the AQP-9 modulator by injection.

In accordance with another embodiment, the carrier is suitable for formulating the AQP-9 modulator in a form suitable for oral intake. The carrier may be a pharmaceutical carrier or a neutraceutical carrier (so as to provide the modulator as a food supplement).

An effective amount of the modulator may be determined by any consideration known to those versed in the art. The amount of the modulator (the inhibitor or inducer) effective to achieve a desired therapeutic result, i.e. treatment of a pathological condition or prevention of same from development, may be varied or adjusted, depending upon the particular application, the delivery system (formulation) of the modulator, the release profile of the modulator from said system, the delivery route, the potency of the particular modulator, and the desired concentration at the treated site, etc. The effective amount is typically determined in appropriately designed clinical trials (dose range studies) and the person versed in the art will know how to properly conduct such trials in order to determine the effective amount. As generally known, an effective amount depends on a variety of factors including the affinity of the modulator to a target site, the selection of delivery system, the distribution profile of the modulator within the body after being administered, a variety of pharmacological parameters such as half life in the body, on undesired side effects, if any, and on other factors such as age and gender of the treated subject, etc.

The pharmaceutical composition comprising the AQP-9 modulator may be administered over an extended period of time in a single daily dose, several doses a day, or on each consecutive day and the like. The treatment period will generally have a length proportional to the length of the disease process and the specific modulator effectiveness and the patient species being treated, all as being appreciated by those versed in the art.

As used herein, the forms "a", "an" and "the" include singular as well as plural references unless the context clearly dictates otherwise. For example, the term "an AQP-9 modulator" includes one or more agents which are capable of specifically affecting AQP-9 activity, thereby fully or partially affecting water/glycerol transport osteoclast influx.

Further, as used herein, the term "comprising" is intended to mean that the composition include the recited API, i.e. AQP-9 modulator, but not excluding other elements, such as physiologically acceptable carriers and excipients as well as other active agents. The term "consisting essentially of" is used to define compositions which include the recited elements but exclude other elements that may have an essential significance on bone modeling (osteoclast formation). "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the AQP-9 modulator as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

NON-LIMITING EXEMPLARY EMBODIMENTS

Cells

Bone marrow cells (BMMs) were prepared from the long bones of 7-9 week old BALB/c male mice. Primary BMMs were prepared by flushing mouse femurs and tibias with α-MEM. Cells were cultured in Petri dishes, in complete α-MEM, supplemented with 10% CMG14-12 culture supernatant, which served as a source of M-CSF. After 3 days of culture, plates were washed 3 to 4 times with PBS to remove non-adherent cells. Adherent cells were removed with trypsin-EDTA solution, centrifuged and resuspended in a fresh medium. Murine macrophage-like RAW264.7 cell line was maintained in RPMI 1640 medium supplemented with 10% fetal calf serum (FCS) in the presence of antibiotics (penicillin and streptomycin). Cells were cultured at 37° C. incubator in a humidified atmosphere with 5% $CO_2$, and media were changed every other day. BMMs ($7\times10^3$/well in α-MEM containing 10% FCS and supernatant from CMG14-12 [1:20]) or RAW264.7 cells ($3\times10^3$/well in RPMI-1640 containing 10% FCS) were incubated in 96-well plates (0.2 ml/well). To induce cells to differentiate into osteoclasts, bacterially-produced recombinant RANKL was added at the time of plating. On day 3, medium was changed and on day 5, osteoclast formation was evaluated (see below).

Tartrate-Resistant Acid Phosphatase (TRAP)

A commercial kit (Cat. No. 387-A, Sigma) was used according to the manufacturer instructions. TRAP-positive cells containing three or more nuclei were scored as osteoclasts.

RNA Extraction and cDNA Preparation

BMMs ($2.5\times10^5$/plate) and RAW 264.7 cells ($1.3\times10^5$/plate) were plated in 35-mm tissue culture plates as described before [Amcheslavsky, A., and Bar-Shavit, Z. (2006) *J. Cell. Physiol.* 207, 244-250]. Total cellular RNA was isolated using EZ-RNA kit (Biological Industries Co., Beit Haemek, Israel) according to the manufacturer's instructions. For RT-PCR, RNA was purified using a DNA-free RNA kit (Zymo Research). The RNA was treated with DNase (RQ1-RNase-free DNase, Promega Corporation, USA) and tested for being essentially DNA-free by a PCR reaction as a negative control. First-strand cDNA was synthesized from 1 µg of total RNA using the Superscript II pre-amplification system (Gibco BRL Life Technologies, UK) according to the manufacturer's instructions. Aquaporins primers sequences and Tm temperature for each gene are shown in Table 1.

TABLE 1

Primers used for the semi-quantitative RT-PCR analysis

| Genebank | Gene name | Primer Forward | Primer Reverse | Tm° |
|---|---|---|---|---|
| NM 007393 | Actin | TGAGAGGGAAATCGTGCGTGA (SEQ ID NO: 1) | TGCTGGAAGGTGGACAGTGA (SEQ ID NO: 2) | 60.0 |
| BC020407 | GAPDH | ATTCAACGGCACAGTCAAGG (SEQ ID NO: 3) | AAGGTGGAAGAGTGGGAGTT (SEQ ID NO: 4) | 57.7 |
| NM022026 | AQP-0 | GAAACCTAGCGCTCAACACG (SEQ ID NO: 5) | ATTGGAGTCACTGGGTCTGG (SEQ ID NO: 6) | 58.7 |
| NM007472 | AQP-1 | TCGTCTTCATCAGCATTGGTT (SEQ ID NO: 7) | CATGCGGTCTGTGAAGTCG (SEQ ID NO: 8) | 57.8 |
| NM 009699 | AQP-2 | CCTTCGAGCTGCCTTCTAC (SEQ ID NO: 9) | TCTTGGTCGAGGGGAACAG (SEQ ID NO: 10)) | 57.2 |
| NM016689 | AQP-3 | CCTCTGGACACTTGGACATGG (SEQ ID NO: 11) | CAGCTTCACATTCTCTTCCTC (SEQ ID NO: 12) | 58.1 |
| NM009700 | AQP-4 | TGGCTCAGAAAACCCCTTAC (SEQ ID NO: 13) | TGTAGCTCCCTTTTGTCTGC (SEQ ID NO: 14) | 56.8 |
| NM009701 | AQP-5 | AAGGAGGTGTGTTCAGTTGCC (SEQ ID NO: 15) | CCTGGTGTTGTGTTGTTGCTG (SEQ ID NO: 16) | 60.0 |
| NM175087 | AQP-6 | TCGCCATCACCTTCAATCTGG (SEQ ID NO: 17) | GAACTTCCCAACAATGACGGC (SEQ ID NO: 18) | 59.9 |
| NM007473 | AQP-7 | TGGCAGCTATCTCGGTGTC (SEQ ID NO: 19) | TGTGGTATGCTGGGGTGAAT (SEQ ID NO: 20) | 58.1 |
| NM007474 | AQP-8 | CTCCGCTCTCTTCATCTTCA (SEQ ID NO: 21) | AGCCTAATGAGCAGTCCTAC (SEQ ID NO: 22) | 55.9 |
| NM022026 | AQP-9 | TTGTGATGGCTCTTTATGCG (SEQ ID NO: 23) | CAGAGTTGAGTCCGAGAGAA (SEQ ID NO: 24) | 55.6 |

Real-Time PCR (RT-PCR)

Primers and probes for the AQP-9, GAPDH, L-32, and MMP9 genes were all Assays-on-Demand products from Applied Biosystems and reactions were set up according to the manufacturer's instructions. Real time PCR was performed in triplicates in 25 µl reactions on the ABI Prism 7000 Sequence Detection System. The relative level of each mRNA was determined using the comparative $C_T$ method for relative quantification using L-32 as an endogenous reference.

Western Blotting

BMMs ($7.5 \times 10^5$/35 mm tissue culture plate) and RAW 264.7 cells ($1.3 \times 10^5$/plate) were plated in 35-mm tissue culture plates as described before [Amcheslavsky, A, (2006), ibid.]. Whole cell lysates were prepared by direct lysis in 200 µl of lysis buffer (10 mM of Tris-HCl, pH 7.4, 150 mM of NaCl, 1 mM of EDTA, 1% Triton X-100, and protease inhibitors [10 ng/ml of aprotinin (Sigma), 10 ng/ml of leupeptin (Sigma), and 50 mM of 4(2-aminoethyl)benzensulfonyl fluoride (AEBSF; Sigma)). 80 µg of lysates were loaded onto 12.5% SDS-polyacrylamide gels. Proteins were transferred onto a nitro-cellulose membrane (Millipore Corporation, Bedford, Mass.) and processed for western blotting. Antibodies were used at the following dilutions: chicken anti-AQP-9 antibody (1:1000, Alpha diagnostic, USA), mouse anti β-actin antibody (1:10000, Alpha diagnostic, USA), goat anti-mouse antibody conjugated to horseradish peroxidase (1:10000, Alpha diagnostic, USA), rabbit anti-chicken antibody conjugated to horseradish peroxidase (1:10000). Immunoreactivity was assayed using an ECL chemiluminescence kit (Pierce Biotechnology, Inc., Rockford, Ill.) according to the manufacturer's instructions.

Surface Area Measurements

The surface area occupied by osteoclasts and their precursors was quantified using a computerized image analysis system (Olympus BX50, DP50, software: ImagePro Plus, Media Cybernetics).

Methylene Blue Uptake

Cells were seeded as for the osteoclast differentiation assay (see above). Monolayers were fixed and methylene blue uptake was measured as described [Goldman, R., and Bar-Shavit, Z. (1979) *J. Natl. Cancer Inst.* 63, 1009-1016].

Data Analysis

All experiments were repeated at least twice, and each experimental treatment was performed with six replications, unless stated otherwise. Data were analyzed with the JMP statistics package (version 4.1, from SAS Institute Inc., Cary, N.C. 27513 USA).

EXAMPLE 1

Aquaporin Expression in Osteoclasts

Using semi-quantitative PCR we measured the expression of aquaporins in osteoclast lineage cells (Table 2). We found that out of 10 aquaporin genes examined, only aquaporin-9 (AQP-9), an aqua-glycerol channel was expressed in osteoclasts and their precursors. RNA preparations obtained from kidney and eye were used as positive controls for certain aquaporins.

TABLE 2

Expression of aquaporins in various mouse cells and tissues

|       | RAW264.7 | Bone marrow | Kidney | Eye |
|-------|----------|-------------|--------|-----|
| AQP-1 | −        | −           | +      | +   |
| AQP-2 | −        | −           | +      | −   |
| AQP-3 | −        | −           | +      | +   |

TABLE 2-continued

Expression of aquaporins in various mouse cells and tissues

|       | RAW264.7 | Bone marrow | Kidney | Eye  |
|-------|----------|-------------|--------|------|
| AQP-4 | −        | −           | −      | +    | −    |
| AQP-5 | −        | −           | −      | −    | n.d. |
| AQP-6 | −        | −           | −      | +    | n.d. |
| AQP-7 | −        | −           | −      | +    | n.d. |
| AQP-8 | −        | −           | −      | +    | n.d. |
| AQP-9 | +        | +           | +      | +    | −    |
| AQP-0 | −        | −           | −      | −    | +    |

+ denotes the presence of RANKL;
− denotes the absence of RANKL;
n.d. denotes not determined

EXAMPLE 2

Increase in AQP-9 Expression in Differentiated Osteoclasts

Figure 1:
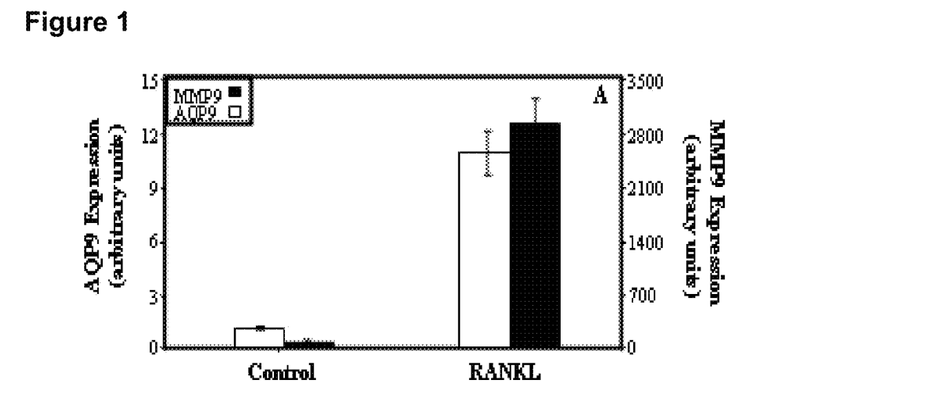
FIG. 1 is a bar graph showing the relative expression of AQP-9 and matrix metalloproteinase-9 (MMP-9) in formed osteoclasts following treatment with RANKL (+RANKL) as compared to non-treated precursor (Control, bone marrow not treated with RANKL)
Figure 2:
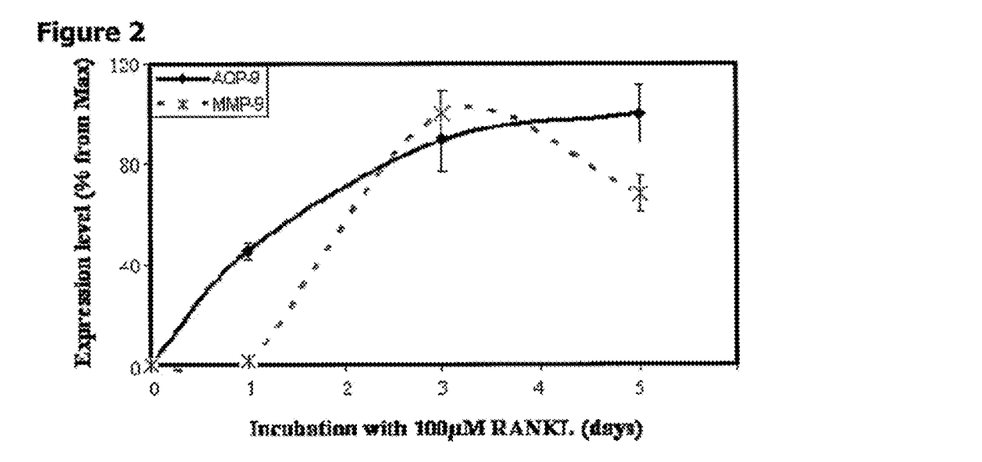
FIG. 2 is a graph showing the kinetics of induction of AQP-9 and MMP-9 expression during osteoclast differentiation by treatment with RANKL. Bars represent the standard error of the mean of at least 4 independent replicates.

The expression of AQP-9 mRNA (using real time PCR) in osteoclasts and in their precursors (FIG. 1) was compared. A dramatic increase in AQP-9 expression was exhibited in osteoclast as compared to the precursors. MMP-9 is served as a marker for the osteoclastic differentiation. Detailed kinetic studies (FIG. 2) of the increase in AQP-9 and MMP-9 expression in response to RANKL showed that the increase in AQP-9 precedes the increase in MMP-9.

Figure 3:
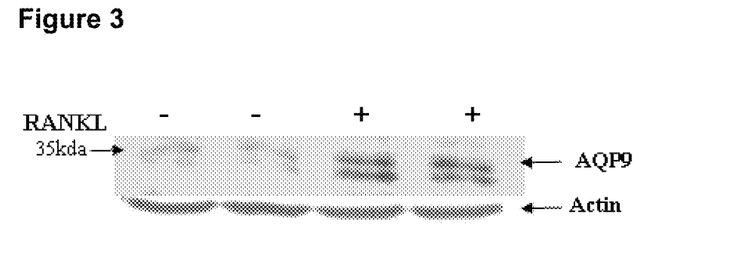
FIG. 3 is a Western blot analysis of AQP-9 in osteoclast lineage cells using anti-AQP-9 and anti-actin antibodies. Two independent samples are presented.
Figure 4A:
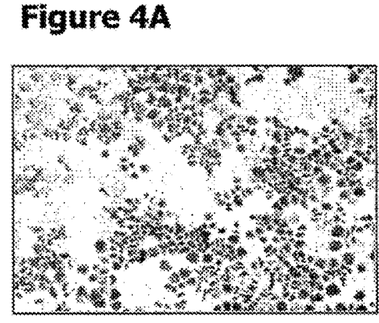
FIGS. 4A-4D are images showing the modulation of osteoclast differentiation by phloretin, following treatment with RANKL (FIGS. 4B and 4D) or without RANKL (FIGS. 4A and 4C) and with 50 µM phloretin (FIGS. 4C and 4D) or without phloretin (FIGS. 4A and 4B)
Figure 4B:
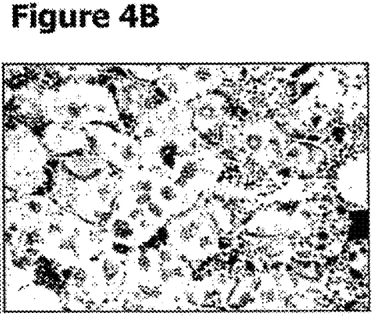
Figure 4C:
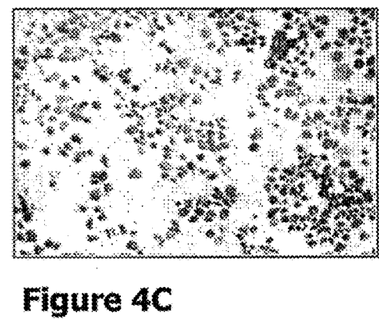
Figure 4D:
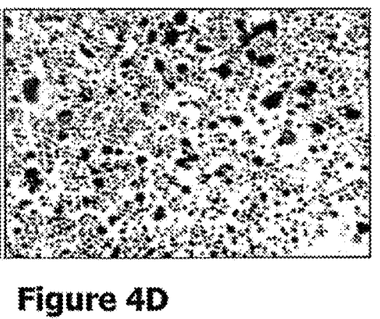

Using specific anti-AQP-9-antibodies (FIG. 3) and western blotting it was shown that the protein expression is greater in osteoclasts (RANKL-treated cells) than in their precursors.

EXAMPLE 3

Aquaporin 9 Activity in Osteoclast Differentiation

In the following assay the significance of the activity of AQP-9 to osteoclast differentiation was determined. To this end, the effect of the AQP-9 inhibitor phloretin (2',4',6'-Tri-hydroxy-3-(4-hydroxyphenyl)-propiophenone on RANKL-induced osteoclast differentiation was examined. Cells were incubated with RANKL for 5 days, and phloretin was added for the last day, when most fusion occurs. (Phloretin stock solution is in DMSO, and therefore DMSO at the amount comparable to the phloretin containing wells was added to the control cultures). A dramatic reduction in osteoclast number (FIG. 4A-4D), and size (FIGS. 4A-4D, Table 3) were observed in cultures containing phloretin.

The inhibitor did not exhibit a significant effect on number (FIG. 4A-4D), and size (FIGS. 4A-4D, right and Table 3) of the mononuclear precursors in cells not treated with RANKL.

TABLE 3

The effect of phloretin on osteoclast lineage cells size (µm²)

|           | −RANKL   | +RANKL          |
|-----------|----------|-----------------|
| Control   | 255 ± 5  | 236323 ± 6170   |
| Phloretin | 267 ± 6  | 23722 ± 4351    |

(Bars represent the standard error of the mean of at least 50 cells per treatment)

The above results demonstrated for the first time the involvement of a specific aquaporin (AQP-9) in the process of osteoclast differentiation: i) AQP-9 is the only aquaporin expressed in osteoclasts and their precursor cell; ii) osteoclast differentiation is associated with a marked increase in AQP-9 expression and finally, iii) inhibition of AQP-9 activity results in inhibition of osteoclast differentiation.

Most cases of pathological bone loss (such as osteoporosis) results from increased osteoclastic activity, and therefore fighting these diseases usually involve inhibition of osteoclast production and activity. We propose therefore, that inhibiting AQP-9 is expected to inhibit pathological bone loss.

Figure 5:
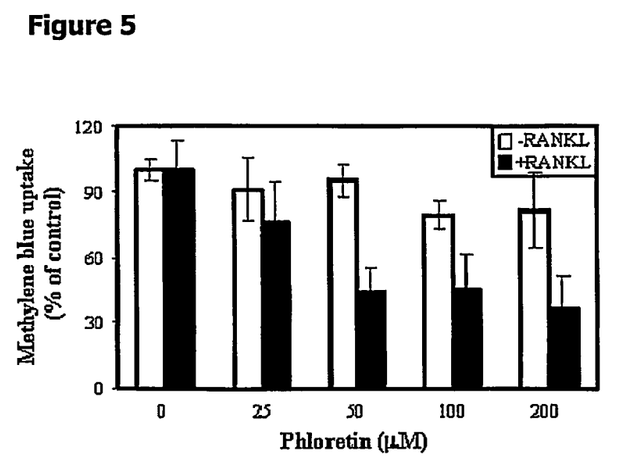
FIG. 5 is bar graph showing the effect of phloretin on methylene blue (MB) uptake in bone marrow cells in the presence or absence of RANKL.

The effect of phloretin on methylene blue uptake is shown in FIG. 5. No effect was observed on mononuclear precursors (BMMs grown in the absence of RANKL). Methylene blue stains both nuclei and cytoplasm and is a reliable measurement of relative cell numbers when there is no difference in cell size between the examined populations. Thus, phloretin does not inhibit mononuclear cell proliferation and size. In contrast, a marked inhibition of methylene blue uptake was observed in RANKL-treated cells, reflecting the decreased cell size.

The invention claimed is:

1. A method of modulating unbalanced osteoclast differentiation, in the treatment of osteoporosis, periodontal disease, aseptic loosening of prosthetic implants, or a bone disease manifested by excess bone loss, the method comprising:
   administering a therapeutically effective amount of phloretin to a subject in need thereof wherein the therapeutically effective amount inhibits aquaporin-9 (AQP-9) activity in one or more of osteoclast cells and osteoclast precursor cells.

2. The method according to claim 1, wherein said osteoclast precursor cells are mononuclear osteoclast cells.

3. The method according to claim 1, wherein the inhibition of the AQP-9 activity is demonstrated by at least one of the following:
   (a) reduction in size of osteoclasts;
   (b) reduction in number of osteoclasts; and
   (c) reduction in number of nuclei in an osteoclast.

4. The method according to claim 1, wherein the phloretin is administered by injecting directly to the subject's bone marrow.

5. The method according to claim 1, wherein the phloretin is administered by injecting into the subject's blood stream.

6. The method according to claim 1, wherein the phloretin is orally administered.

7. A method for treating osteoporosis, periodontal disease, or aseptic loosening of prosthetic implants, in a subject, comprising:
   administering a therapeutically effective amount of a pharmaceutical composition comprising phloretin and a pharmaceutically acceptable carrier to the subject in need thereof, wherein the therapeutically effective amount inhibits AQP-9 activity in one or more of osteoclast cells and osteoclast precursor cells.

8. The method according to claim 7, wherein the pharmaceutical composition is administered by injecting directly to the subject's bone marrow.

9. The method according to claim 7, wherein the pharmaceutical composition is administered by injecting into the subject's blood stream.

10. The method according to claim 7, wherein the pharmaceutical composition is orally administered.

* * * * *

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial sequence
<220> FEATURE:
<223> OTHER INFORMATION: Primer forward derived from Mus musculus Actin,
      Genebank accession no. NM_007393

<400> SEQUENCE: 1
tgagagggaa atcgtgcgtg a                                              21

<210> SEQ ID NO 2
<211> LENGTH: 20
<212> TYPE: DNA
<213> ORGANISM: Artificial sequence
<220> FEATURE:
<223> OTHER INFORMATION: Primer reverse derived from Mus musculus Actin,
      Genebank accession no. NM_007393

<400> SEQUENCE: 2
tgctggaagg tggacagtga                                                20

<210> SEQ ID NO 3
<211> LENGTH: 20
<212> TYPE: DNA
<213> ORGANISM: Artificial sequence
<220> FEATURE:
<223> OTHER INFORMATION: Primer forward derived from Mus musculus GAPDH,
      Genebank accession no. BC020407

<400> SEQUENCE: 3
attcaacggc acagtcaagg                                                20

<210> SEQ ID NO 4
<211> LENGTH: 20
<212> TYPE: DNA
<213> ORGANISM: Artificial sequence
<220> FEATURE:
<223> OTHER INFORMATION: Primer reverse derived from Mus musculus GAPDH,
      Genebank accession no. BC020407

<400> SEQUENCE: 4
aaggtggaag agtgggagtt                                                20

<210> SEQ ID NO 5
<211> LENGTH: 20
<212> TYPE: DNA
<213> ORGANISM: Artificial sequence
<220> FEATURE:
<223> OTHER INFORMATION: Primer forward derived from Homo sapiens AQP-0,
      Genebank accession no. NM_022026

<400> SEQUENCE: 5
gaaacctagc gctcaacacg                                                20
```

```
<210> SEQ ID NO 6
<211> LENGTH: 20
<212> TYPE: DNA
<213> ORGANISM: Artificial sequence
<220> FEATURE:
<223> OTHER INFORMATION: Primer reverse derived from Homo sapiens AQP-0,
      Genebank accession no. NM_022026

<400> SEQUENCE: 6
attggagtca ctgggtctgg                                                   20

<210> SEQ ID NO 7
<211> LENGTH: 21
<212> TYPE: DNA
<213> ORGANISM: Artificial sequence
<220> FEATURE:
<223> OTHER INFORMATION: Primer forward derived from Homo sapiens AQP-1,
      Genebank accession no. NM_007472

<400> SEQUENCE: 7
tcgtcttcat cagcattggt t                                                 21

<210> SEQ ID NO 8
<211> LENGTH: 19
<212> TYPE: DNA
<213> ORGANISM: Artificial sequence
<220> FEATURE:
<223> OTHER INFORMATION: Primer reverse derived from Homo sapiens AQP-1,
      Genebank accession no. NM_007472

<400> SEQUENCE: 8
catgcggtct gtgaagtcg                                                    19

<210> SEQ ID NO 9
<211> LENGTH: 19
<212> TYPE: DNA
<213> ORGANISM: Artificial sequence
<220> FEATURE:
<223> OTHER INFORMATION: Primer forward derived from Homo sapiens AQP-2,
      Genebank accession no. NM_009699

<400> SEQUENCE: 9
ccttcgagct gccttctac                                                    19

<210> SEQ ID NO 10
<211> LENGTH: 19
<212> TYPE: DNA
<213> ORGANISM: Artificial sequence
<220> FEATURE:
<223> OTHER INFORMATION: primer reverse derived from Homo sapiens AQP-2,
      Genebank accession no. NM_009699

<400> SEQUENCE: 10
tcttggtcga ggggaacag                                                    19

<210> SEQ ID NO 11
<211> LENGTH: 21
<212> TYPE: DNA
<213> ORGANISM: Artificial sequence
<220> FEATURE:
<223> OTHER INFORMATION: Primer forward derived from Homo sapiens AQP-3,
      Genebank accession no. NM_016689

<400> SEQUENCE: 11
cctctggaca cttggacatg g                                                 21
```

-continued

<210> SEQ ID NO 12
<211> LENGTH: 21
<212> TYPE: DNA
<213> ORGANISM: Artificial sequence
<220> FEATURE:
<223> OTHER INFORMATION: Primer reverse derived from Homo sapiens AQP-3,
    Genebank accession no. NM_016689

<400> SEQUENCE: 12
cagcttcaca ttctcttcct c                                              21

<210> SEQ ID NO 13
<211> LENGTH: 20
<212> TYPE: DNA
<213> ORGANISM: Artificial sequence
<220> FEATURE:
<223> OTHER INFORMATION: Primer forward derived from Homo sapiens AQP-4,
    Genebank accession no. NM_009700

<400> SEQUENCE: 13
tggctcagaa aaccccttac                                                20

<210> SEQ ID NO 14
<211> LENGTH: 20
<212> TYPE: DNA
<213> ORGANISM: Artificial sequence
<220> FEATURE:
<223> OTHER INFORMATION: Primer reverse derived from Homo sapiens AQP-4,
    Genebank accession no. NM_009700

<400> SEQUENCE: 14
tgtagctccc ttttgtctgc                                                20

<210> SEQ ID NO 15
<211> LENGTH: 21
<212> TYPE: DNA
<213> ORGANISM: Artificial sequence
<220> FEATURE:
<223> OTHER INFORMATION: Primer forward derived from Homo sapiens AQP-5,
    Genebank accession no. NM_009701

<400> SEQUENCE: 15
aaggaggtgt gttcagttgc c                                              21

<210> SEQ ID NO 16
<211> LENGTH: 21
<212> TYPE: DNA
<213> ORGANISM: Artificial sequence
<220> FEATURE:
<223> OTHER INFORMATION: Primer reverse derived from Homo sapiens AQP-5,
    Genebank accession no. NM_009701

<400> SEQUENCE: 16
cctggtgttg tgttgttgct g                                              21

<210> SEQ ID NO 17
<211> LENGTH: 21
<212> TYPE: DNA
<213> ORGANISM: Artificial sequence
<220> FEATURE:
<223> OTHER INFORMATION: Primer forward derived from Homo sapiens AQP-6,
    Genebank accession no. NM_175087

<400> SEQUENCE: 17
tcgccatcac cttcaatctg g                                              21

<210> SEQ ID NO 18

```
<211> LENGTH: 21
<212> TYPE: DNA
<213> ORGANISM: Artificial sequence
<220> FEATURE:
<223> OTHER INFORMATION: Primer reverse derived from Homo sapiens AQP-6,
      Genebank accession no. NM_175087

<400> SEQUENCE: 18
gaacttccca acaatgacgg c                                              21

<210> SEQ ID NO 19
<211> LENGTH: 19
<212> TYPE: DNA
<213> ORGANISM: Artificial sequence
<220> FEATURE:
<223> OTHER INFORMATION: Primer forward derived from Homo sapiens AQP-7,
      Genebank accession no. NM_007473

<400> SEQUENCE: 19
tggcagctat ctcggtgtc                                                 19

<210> SEQ ID NO 20
<211> LENGTH: 20
<212> TYPE: DNA
<213> ORGANISM: Artificial sequence
<220> FEATURE:
<223> OTHER INFORMATION: Primer reverse derived from Homo sapiens AQP-7,
      Genebank accession no. 007473

<400> SEQUENCE: 20
tgtggtatgc tggggtgaat                                                20

<210> SEQ ID NO 21
<211> LENGTH: 20
<212> TYPE: DNA
<213> ORGANISM: Artificial sequence
<220> FEATURE:
<223> OTHER INFORMATION: Primer forward derived from Homo sapiens AQP-8
      Genebank accession no. NM_007474

<400> SEQUENCE: 21
ctccgctctc ttcatcttca                                                20

<210> SEQ ID NO 22
<211> LENGTH: 20
<212> TYPE: DNA
<213> ORGANISM: Artificial sequence
<220> FEATURE:
<223> OTHER INFORMATION: Primer reverse derived from Homo sapiens AQP-8,
      Genebank accession no. NM_007474

<400> SEQUENCE: 22
agcctaatga gcagtcctac                                                20

<210> SEQ ID NO 23
<211> LENGTH: 20
<212> TYPE: DNA
<213> ORGANISM: Artificial sequence
<220> FEATURE:
<223> OTHER INFORMATION: Primer forward derived from Homo sapiens AQP-9,
      Genebank accession no. NM_022026

<400> SEQUENCE: 23
ttgtgatggc tctttatgcg                                                20

<210> SEQ ID NO 24
<211> LENGTH: 20
```

```
<212> TYPE: DNA
<213> ORGANISM: Artificial sequence
<220> FEATURE:
<223> OTHER INFORMATION: Primer reverse derived from Homo sapiens AQP-9,
      Genebank accession no. NM_022026

<400> SEQUENCE: 24
cagagttgag tccgagagaa                                                    20
```